US005807750A

United States Patent [19]
Baum et al.

[11] Patent Number: 5,807,750
[45] Date of Patent: Sep. 15, 1998

[54] OPTICAL SUBSTANCE ANALYZER AND DATA PROCESSOR

[75] Inventors: Marc M. Baum; Harry C. Lord, both of Baldwin Park, Calif.

[73] Assignee: Air Instruments and Measurements, Inc., Baldwin Park, Calif.

[21] Appl. No.: 434,527

[22] Filed: May 2, 1995

[51] Int. Cl.$^6$ .................. G01N 21/00; G01N 21/01; G01N 21/35

[52] U.S. Cl. ............... 436/164; 250/341.1; 356/436; 422/82.05; 422/82.09; 422/82.11; 422/83; 436/171

[58] Field of Search .................. 422/82.05, 82.09, 422/82.11, 83; 436/164, 171; 250/341, 373; 356/436

[56] References Cited

U.S. PATENT DOCUMENTS

| | | | |
|---|---|---|---|
| 3,819,945 | 6/1974 | Egan et al. | 250/373 |
| 4,403,861 | 9/1983 | Boisde et al. | 356/407 |
| 4,664,522 | 5/1987 | LeFebre | 356/328 |
| 4,746,218 | 5/1988 | Lord, III | 356/437 |
| 4,786,171 | 11/1988 | LeFebre et al. | 356/326 |
| 4,801,805 | 1/1989 | Butler et al. | 250/343 |
| 5,070,246 | 12/1991 | Durham et al. | 250/373 |
| 5,184,193 | 2/1993 | LeFebre | 356/325 |
| 5,272,345 | 12/1993 | Durham et al. | 250/373 |

FOREIGN PATENT DOCUMENTS

| | | |
|---|---|---|
| 631137 | 12/1994 | European Pat. Off. . |
| 60-205336 | 10/1985 | Japan . |

OTHER PUBLICATIONS

R.A. Morton et al. *Analyst* 1946, 71, 348–356.
M.T. Perlstein et al. *Microchem. J.*, 1976, 21, 485–495.
D.A. Noe et al. *Clin. Chem.* 1984, 30, 627–630.
L.A. Pyles et al. *Proc. Soc. Exp. Biol. Med.* 1993, 202, 407–419.
S. Wold et al. *J. Chemometrics* 1987, 1, 41–56.
S. Foulk et al. *Am. Lab.* 1987, 19, 52–53.
M. Gerritsen et al. *Chemomet. Intellig. Lab. Sys.* 1992, 15, 171–184.
S.J. Kahlei et al. *Adv. Instrum. Control* 1992, 47, 1287–1294.
M.C. Pascual–Marti et al. *Fresenius J Anal. Chem.* 1993, 347, 305–313.
Translation of JP 60–205 336.
S. Wold et al. *Chem. Abstr.* 1987, 106, 226419n.
L.G. Weyer et al. *Appl. Spectrosc.* 1987, 41, 786–790.
S. Foulk et al. *Chem. Abstr.* 1988, 108, 87201m.
J. Workman *Chem. Abstr.* 1989, 111, 104586x.
M. Otto *Analyst* 1990, 115, 685–688.
M. Gerritsen et al. *Chem. Abstr.* 1992, 117, 225280a.
I. Duran–Meras et al. *Analyst* 1993, 118, 807–813.

(List continued on next page.)

*Primary Examiner*—Arlen Soderquist
*Attorney, Agent, or Firm*—David O'Reilly

[57] ABSTRACT

A liquid and gas analyzing system that provides a sample collecting probe that delivers the sample through inert materials to prevent any contamination. For gas analyzing for environmental monitoring process control, a sample collecting probe having a borosilicate glass tube liner connected through an inner spiral tube to the analyzer prevents contamination. The system then delivers the sample to a single pass radiated optical cell by a light beam. The light beam is collected by a miniature CCD array spectrometer and delivered to an industrial PC. The output from the industrial PC is then delivered to a software controlled data acquisition system for analysis. The system is constructed to be a modular in design allowing addition of complementary components for measuring and analyzing different materials. The system described can be used for extractive gas analysis as well as extractive liquid analysis for monitoring stack gases, environmental air or general environmental monitoring and with modifications for breath analysis and human saliva and blood testing. The system is also adaptable for long path remote sense gas monitoring of fence lines and for leak detection.

43 Claims, 7 Drawing Sheets

OTHER PUBLICATIONS

S.J. Kahle et al. *Chem. Abstr.* 1993, 119, 55557t.
V. Cerda et al. *Chem. Abstr.* 1993, 119, 261744e.
M.C. Pascual–Marti et al. *Chem. Abstr.* 1994, 120, 68513w.
K.J. Schlager et al. *Chem. Abstr.* 1994, 120, 181679t.
A. Espinosa–Mansilla et al. *Analyst*, 1994, 119, 1183–1188.
E. Bratz et al. *Chem. Abstr.* 1994, 121, 124103x.
J.H. Cho et al. *Anal. Chem.* 1995, 67, 2858–2863.

OPTICAL SUBSTANCE ANALYZER AND DATA PROCESSOR

BACKGROUND OF THE INVENTION

1. Field of the Invention

This invention relates to devices for detecting and measuring the chemical composition of gaseous and liquid compounds, and more particularly, relates to an analyzer for analyzing gas and liquid compounds utilizing ultraviolet, visible and infrared absorption spectroscopy.

2. Background Information

Liquid and gas analyzers are being used to analyze the composition of compounds for purposes of environmental monitoring and control, as well as medical and diagnostic purposes. Low level detection and measurement of gaseous and liquid compounds is currently being achieved through a variety of different analytical techniques including spectroscopy, mass spectrometry, gas chromatography and electro chemical cells. The need to measure increasingly lower concentrations of pollutants in waste stream produced by industry, as well as in the environment, is being catalyzed by stricter environmental regulations. Industrial plants seek to optimize the process efficiencies requiring fast feedback from the monitoring instruments to make necessary control adjustments. A genuine need for low cost, sensitive and fast analyzing exists. The monitoring of gaseous analytes is described in more detail in "Air Monitoring by Spectrascopic Techniques" (Ed Markus W. Sigrist, 1994 Wiley-Interscience, John Wiley and Sons, New York, Chitchester, Brisbane, Toronto, Singapore).

It is therefore, one object of the present invention to provide a gaseous and liquid analyzer for use in environmental monitoring and process control.

Yet another object of the present invention is to provide a liquid and gas analyzer that can be used in the bio-medical industry for diagnostic purposes.

Still another object of the present invention is to provide a liquid and gas analyzer using ultraviolet (UV) based Differential Optical Absorption Spectroscopy (DOAS) analysis.

Yet another object of the present invention is to provide a liquid and gas analyzing system having a short path coupled to monitor exhaust gas streams by extractive multi-gas analysis.

Still another object of the present invention is to provide a liquid and gas analyzer for monitoring extreme low levels of gases at a utility for environmental compliance and process control.

Yet another object of the present invention is to provide a liquid and gas analyzer that utilizes extractive gas analysis system for monitoring ambient air quality.

Still another object of the present invention is to provide a liquid and gas analyzer that provides in-situ gas analysis employing fiber optics.

Yet another object of the present invention is to provide a liquid and gas analyzer that utilizes extractive liquid analysis for environmental monitoring.

Yet another object of the present invention is to provide a liquid and gas analyzer that provides in-situ liquid analysis for environmental monitoring.

Still another object of the present invention is to provide a liquid and gas analyzing system that provides long path/remote sensing gas monitoring such as fence line monitoring and leak detection.

Yet another object of the present invention is to provide a liquid and gas analyzing system that can be utilized for non-invasive human breath analysis using conventional sterile plastic bags fitted with a valve for a sample collection.

Still another object of the present invention is to provide a liquid and gas analyzing system that employs a fiber optic based system for analysis of human fluids such as saliva, human blood or urine.

BRIEF DESCRIPTION OF THE INVENTION

The purpose of the present invention is to provide efficient liquid and gas analyzing system that can be employed both in environmental monitoring and process control, and also has medical applications.

A variety of unique features are embodied in the liquid and gas analyzer of the present invention that make is stand out from contemporary systems. The system, among other things, employs an extractive analyzer for measurement of low levels of gases and incorporates features that allow use in extreme applications such as high temperatures and with highly corrosive chemicals. One embodiment allows use in industrial enterprises that typically need to monitor low levels, often zero to ten parts per million (ppm) of ammonia ($NH_3$), nitrous oxide (NO) and sulfur dioxide ($SO_2$) in a gas stream exhausting from boilers.

The combustion of fossil fuels, used for whatever purpose, leads to high temperatures often generating NO, $NO_2$ and $SO_2$ amongst others. Oxides of nitrogen ($NO_x$) can be reduced by controlling the injection of $NH_3$ (either in the form of free gas or as urea) into a stack gas treatment system, leading to a reaction affording water and nitrogen. However, the penetration of $NH_3$ into the gas treatment system and subsequently into the environment (often referred to as $NH_3$ slip) is highly undesirable. The gas analyzer of the present invention, therefore, can continuously monitor the emitted extreme low concentration of these compounds in a sufficiently short period of time (in the order of seconds) to allow feedback and process control.

The system of the present invention utilizes a sampling probe comprised of a borosilicate gas tube liner surrounded by an electrical heater (controlled to maintain the temperature at 250° C.) and a protective 316 stainless steel sheath. The tip of the probe is provided with a probe filter (sintered quartz, 2 μm) glass blown onto a medium wall ½ inch tubing so that a sample is filtered at the sampling point rather than inside the probe housing outside the stack as with traditional probes. The probe tip is protected with a steel funnel. The borosilicate probe lining is constructed so that it can be easily replaced in the field.

The end of the borosilicate probe liner extends out of the stack and is connected to a T-union of synthetic inert material in the probe housing. The T-union is linked to a commercially available automated cylinder gas calibration unit by a high temperature solenoid valve lined with inert material. A third connection to the T-union is comprised of a specially formed piece of tubing made of an inert synthetic material in a spiral configuration to minimize stress on glass pieces. The probe housing and tubing is insulated, heated, and temperature regulated to approximately 250° C. and is delivered to an analyzer.

In the analyzer, the heated line is connected to a borosilicate T-piece via a synthetic inert union. A vertical portion of the T-piece is connected to a source of compressed air (blow back) through a suitable solenoid valve to periodically clean the probe filter of particulates. The third end of the T-piece is an all glass solenoid valve (ball and socket design with a metal plunger encapsulated in glass) that allows the analyzer to be isolated during blow back of compressed air or if a system failure occurs. A sample cell is then connected via a synthetic union to the downstream end of the solenoid valve (½ inch glass tubing). A heated pump aspirates the gas sample downstream from the sample cell which is then vented to the cabinet exhaust. The entire sampling system is surrounded by a special electric heater and is insulated as is known in the art. Temperature sensors, fitted at strategic points throughout the system, monitor and control the temperature at a specified temperature such as at 250° C. up to and including the optical cell and at 150° C. at the exhaust vent from the cell. The entire analyzing system can be stack mounted or mounted on a surface close to the stack.

A preferred feature of the invention is to have the analyzer on the stack by the probe, eliminating the need for long sample lines that are costly and difficult to maintain, and inevitably lead to sample loss/contamination. The sample volume between the probe tip and the analyzer exhaust being taken is under one liter, leading to very fast response time. Also, none of the gas sample is exposed to any metal surface from the point of sampling to the exhaust from the optical cell in the analyzer. The main contact is with borosilicate glass at 250° C., a material that inert to into the gases and the mixture as well as possessing low adsorption properties. The system described allows a non-corrupted, representative gas sample to be delivered to an optical cell in a very short period of time using a low maintenance and low cost sampling system.

The optical sample cell in the analyzer is a single pass design having two fused silica windows made of quartz. Fast off-axis mirrors are employed at each end of the cell to allow optimum interface between the various components as well as good beam collimation. Once aligned, the system is rugged and insensitive to mechanical vibrations. In some instances, a multi-pass cell could be used instead of a single-pass design allowing even longer optical path lengths and hence higher sensitivity.

The sample cell is selected to fit the application. It is either a heated cell or an ambient temperature cell. The cell has a fixed optical path length that is typically selected to be between 1 and 20 meters, but optical path lengths of more than 100 meters are possible allowing sample measurements to the low ppb levels. The use and operation of multi-pass sample cells is described in "Gas Measurement in the Fundamental Infrared Region, Volume 1" by Philip Hanst and Steven Hanst.

Another option would permit the mirrors to be dispensed with altogether by using a "light tube" design. In this embodiment, the entire optical cell is externally coated with a reflective material. The illumination or radiation source is then placed close to the entrance of the cell with a detector directly in-line at the opposite end. This system eliminates the need for any lenses or mirrors. The angle of the source, to the cell, could be varied to change the number of reflections the light beam would make inside the cell, which would change the distance traveled by the beam. It should be noted that a cell coated with a reflective surface would have an effective optical path length that is longer than the physical length of the cell, thereby raising the instrument sensitivity. Undesirable radiation can be filtered out using bandpass filters.

The radiation source for the cell is preferably a xenon flash lamp, supplied with trigger module and power supply. This type of radiation is preferred because it has a strong emission in the desired spectral range and is very stable. Another advantage of this source of radiation is that typical emission peaks from the excited xenon gas can be used to calibrate the detector and test optical resolution of the system. The trigger module for the system is under direct control of software controlling the spectrometer, thereby synchronizing the energy pulse with measurements. Alternate radiation sources can be a deuterium lamp, mercury lamp, mercury/argon lamp, tungsten halogen lamp, diode laser, helium-neon laser, etc. if desired.

A detector receives the radiation passing through the sample and is comprised of a miniature spectrometer which is a dispersive instrument of a particular design equipped with an array of detectors. The miniature spectrometer detector has a measurement range from 180 to 300 nm (nanometer). Additional miniature spectrometers can be added in a modular fashion to increase the measurement range without sacrificing optical resolution and/or to act as a reference channel. The system is constructed so that a plurality of detectors in the miniature spectrometer all receive their respective wavelengths of radiation simultaneously so that the time related effects of the flowing sample will not introduce inaccuracies into the measurement.

The output of the miniature spectrometer is connected to an analog to digital converter and custom data acquisition system having software that has been written to accommodate the requirements of the analyzer. The output of the spectrometer is in the form of electronic counts as a function of spectral wavelength. This information is treated mathematically to filter instrument noise to achieve higher detection limits and account for interferences by other species in the sample. The software processes the data by first obtaining an electronic count value of the wavelength set characteristic of a sample. A signal ratio for the sample is then calculated that minimizes spectral interferences. Environmentally derived algorithms are then used to calculate the concentration of the sample from instrument's response, the concentration of spectral interference, and the extent of interaction of spectral interference on the concentration of the sample. The interference is then subtracted from the initial concentration to give a first approximation. A second interference-free approximation is performed by using a decision matrix and a corresponding experimentally determined step-by-step procedure. The output provides an accurate analysis and measurement of extremely low levels of components in the sample.

A unique aspect of the invention is its modular construction that allows the addition of other components to make the system highly versatile and powerful. An infrared (IR) analyzer module can easily be interfaced with the sample and analyzing system. The heated gas stream would be fed from the pump exhaust through a heated multi-pass cell and then connected to either a miniature gas chromatographic instrument or vented to the atmosphere or back into the stack. The principle of an IR component of this system is shown and described in U.S. Pat. No. 4,746,218 of Lord, issued May 24, 1988, incorporated herein by reference. The source could also consist of a glowing ceramic element, a diode laser and/or a carbon dioxide laser.

Several options are available to replace the gas filtration and detection system such as a dispersive Fourier Transform (FT) spectrometer, a rotating diffraction grating mounted to a synchronous motor, a linear circular variable filter, a photo acoustic spectroscopy system or an opto-acoustic filtration system.

Another option is the addition of gas chromatography capability. This option permits the use of a miniature gas chromatographic (GC) instrument that can be easily linked into the system either instead of, or along with the IR capabilities described above. The chromatographic instrument would be connected in parallel with the sample line and would be programmed to sample the gas stream at regular intervals.

The system also has applications in the biomedical industry. It would provide a system that would yield a versatile, non-invasive diagnostic system having vast potential. One such application would be as a breath analyzer.

The breath of healthy humans and animals normally contains approximately 60 to 80 volatile compounds produced by endogenous metabolic and catabolic reactions. Individual breath components have yielded valuable information as disease indicators. The difference in the system is that sample handling temperatures would be around 40° C. Also, instead of a probe, a pass-through or re-breathing system could be employed to collect the breath samples. A sample would be collected in a sterile, sealed bag made of an inert synthetic material fitted with a suitable valve. The valve would then be connected to the analyzer for sampling. This system sampling would be static in contrast to the dynamic sampling of stack gases.

The gas mixture would be analyzed and then purged with zero gas. Multiple measurements would be possible in a short period of time from one sample of breath thereby allowing an internal check of the measured concentration of a target analyte. An analyte is a chemical species, either an atom, molecule, radical or ion, in a fluid which can be gaseous or liquid. Optionally, a more elegant sampling could be provided by having the patient breathe directly into the analyzer which would be equipped with a low power pump to ensure adequate sample turnover rates and draw a zero gas through the system once measurements have been made.

Another medical application would be for the analysis of human fluids such as saliva, blood and urine. Human saliva contains a variety of compounds that as in the case of human breath, have a variety of applications for non-invasive diagnostics. Human blood, of course, also has a well documented history of diagnostic value. The measurements of saliva, human blood or urine would also be made in a static mode. The sample being analyzed would be transferred to a disposable cell and inserted into a slot provided in the analyzer. In the case of blood analysis the sample would probably require an anaerobic handling. Once placed in the analyzer, the sample would be analyzed by the same steps previously described.

The above and other novel features of the invention will be more fully understood from the following detailed description and the accompanying drawings, in which:

DETAILED DESCRIPTION OF THE INVENTION

Figure 1A:
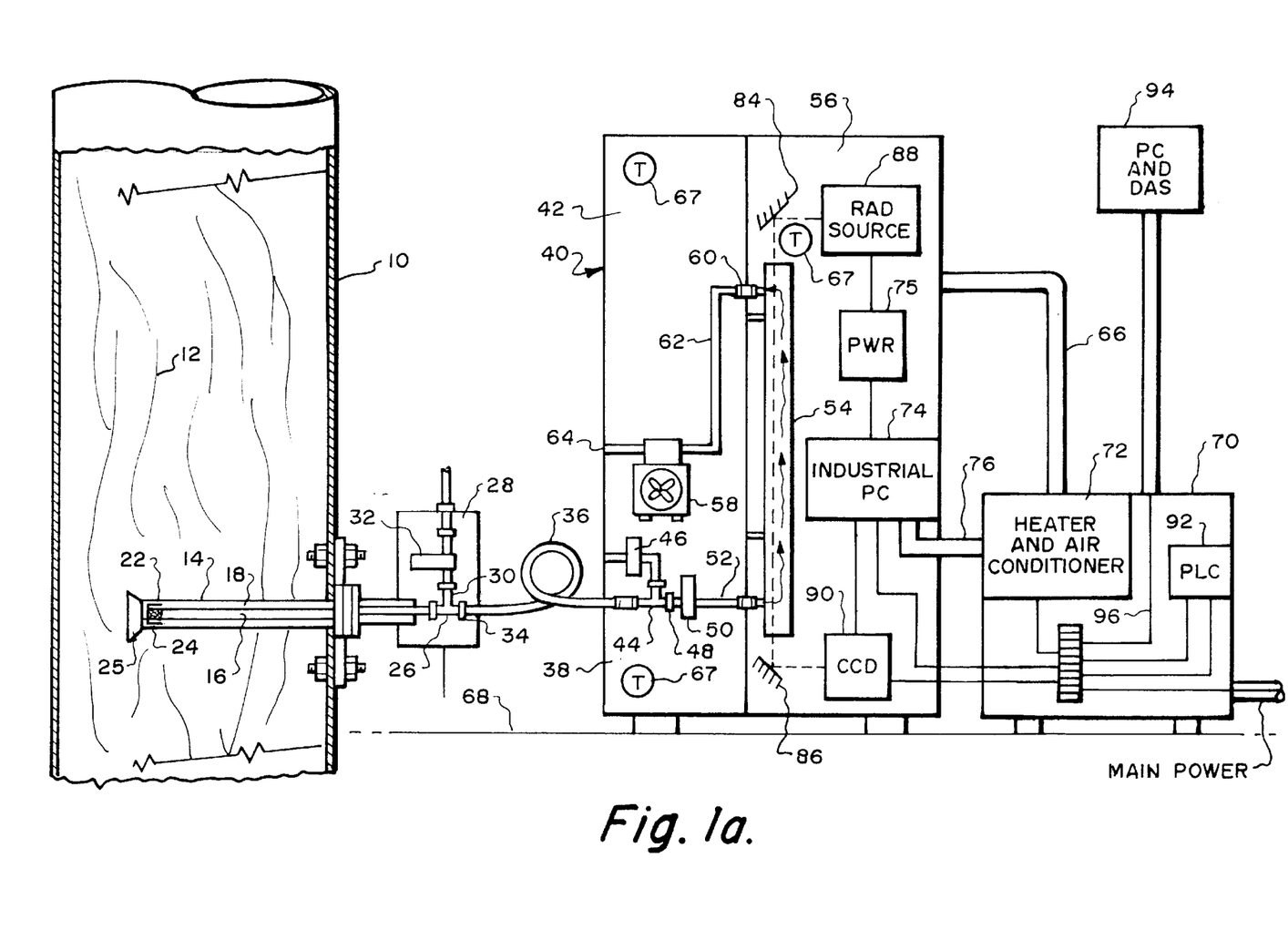
FIG. 1(a) is a diagram of a stack analyzing system constructed according to the invention.
Figure 1B:
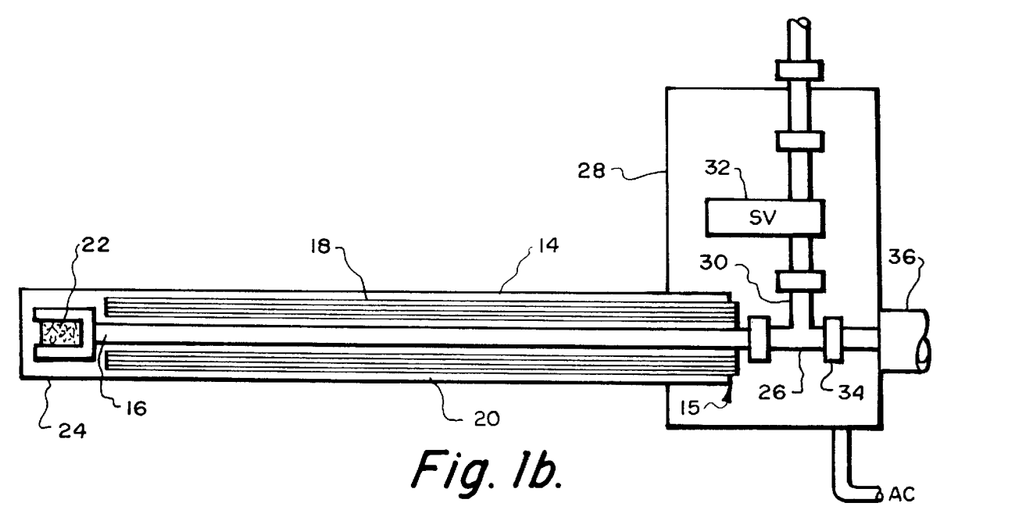
FIG. 1(b) is a diagram of a probe assembly for use in the stack analyzing system.
Figure 2:
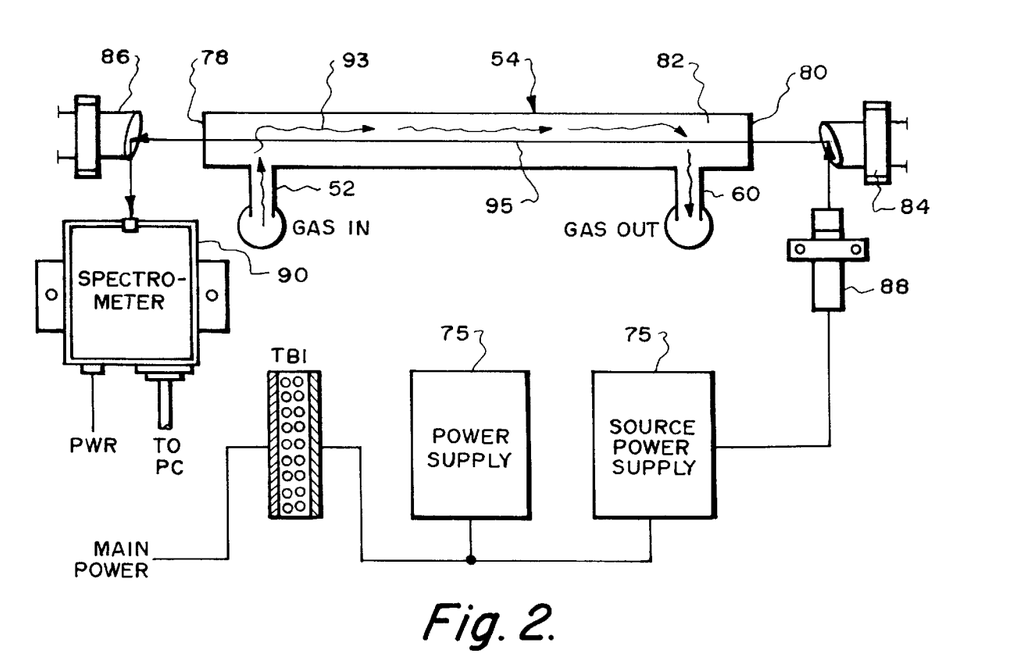
FIG. 2 is a diagrammatic view of the optical system for use in the liquid and gas analyzing system according to the invention.

FIGS. 1 and 2 are diagrams illustrating one embodiment of the invention installed to measure the concentration of selected gases in a stack. FIGS. 1 and 2 are illustrative of the unique features of the invention that allow short coupled (i.e., less than about ten feet) extractive testing of gas streams in a stack and analysis in the system that is modular in construction. A gas stream 12, exhausting from stack 10 results from the combustion of fossil fuels to drive various processes, before being exhausted in the atmosphere. Stack 10 will be a conduit from which the gas stream 12 flows. The system shown is not limited to the analysis of a gas stream 12 in a stack 10, but can be used for extractive gas analysis to monitor ambient air quality, in-situ gas analysis employing fiber optics and extractive or in-situ liquid analysis for environmental monitoring. It is also applicable through long pass/remote sensing gas monitoring (e.g., for fence line monitoring and leak detection). In all of the above applications involving gases, the system is designed in a modular fashion to integrate into complementary multi-gas non-dispersive and/or dispersive infrared analyzers.

Probe 14, illustrated in FIGS. 1a and 1b, is mounted in the wall of stack 10 for extracting a gas sample. Sampling probe 14 is comprised of a borosilicate glass liner 16 surrounded by an electrical heater 18 and protected by a "316" stainless steel sheath 20. Heater 18 maintains the temperature of liner 16 at approximately 250° C. Probe filter 22 is of a sintered quartz, 2 μm glass blown into the medium walled ½ inch tubing 24 that makes up the tip of probe 14 in stack 10 so that samples are filtered at the sampling point inside the probe housing rather than outside the stack as with usual probes. A stainless steel funnel 25 protects the tip of probe 14. The probe is manufactured so that borosilicate probe liner 16 can be easily replaced in the field.

Out of stack end of borosilicate probe liner 16 is connected to T-union 26 of a synthetic inert material in probe housing 28. Vertical connection 30 of T-union 26 is comprised of a short piece of inert material followed by a lined high temperature solenoid valve 32, linking the system to an automated gas calibration device (not shown). Outlet 34 of T-union 26 connects to a specially formed piece of flexible tubing 36 made of inert material. Flexible tubing 36 is formed in a spiral to minimize stress on the glass line 52 and is heated, insulated and temperature regulated to 250° C. and is connected to chamber 38 of analyzer 40.

Analyzer 40 is designed to allow the system to be constructed in a modular fashion to integrate complementary components. For example, the system is designed so that a complementary multi-gas non-dispersive infrared (NDIR) analyzer or other components can be easily integrated, as will be described in greater detail hereinafter. Chamber 42 allows the addition of integrated additional components.

Heated flexible tubing 36 connects to borosilicate T-piece 44 via a synthetic inert union. The vertical portion of T-piece 44 connects through a suitable solenoid valve 46 to receive a source (not shown) of compressed air (blow back) to periodically clear probe filter 22 of particles. Compressed air is forced backwards through the system through probe 14 and filter 22 to clear probe filter 22. Outlet end 48 of T-piece 44 that is glass blown is connected to a unique all glass solenoid valve (ball and socket design with a metal plunger encapsulated in glass) such as Model No. G-170 manufactured by Glass Instruments, Inc. Solenoid valve 50 allows the analyzer to be isolated during blow back or if system failure occurs.

Solenoid valve 50 is connected directly to sample cell 54 by a inert union 52 (½ inch glass tubing). Pump 58 draws sample from exit 60 through tubing 62 which is then exhausted through port 64. Electric heater 66 surrounds the entire sampling system, and is insulated. Several temperature sensors 67 (not shown) are fitted at strategic points (e.g., in each chamber 38, 42, 56) in the system to monitor and control temperature at 250° C. up to and including optical cell 54 and at 150° C. up to exhaust vent 64 from analyzer cabinet 40.

The entire analyzer can either rest on floor 68 adjacent to stack 10 or can be mounted directly on the stack by a specially designed bracket (not shown) that bolts to standard size flanges. The entire analyzer is near the stack by probe 14 thereby eliminating the need for long sample lines which are costly, difficult to maintain and inevitably lead to sample loss/contamination. The sample line in the present system need not be any longer than about ten feet and will generally be no more than about three feet.

The volume of the entire sampling and analyzing system is under one liter, thereby leading to very fast response times. The gas sample collected by probe 14 is not exposed to any metal surface at the point of sampling at filter 22 up to exhaust 60 from detector optical cell 54. The main contact of the entire sample received by probe 14 is borosilicate glass and/or quartz, a material that is inert to the gas in the mixture and possesses low adsorptive properties. As a result of the above conditions, the construction of the sample system with entirely inert materials, and the proximity of the analyzing system, a non-corrupted representative gas sample is delivered to the detector optical cell 54 over a very short period of time using a low maintenance and low cost sampling system.

Cabinet 70 contains a heater 72 for heating the system and an air conditioner to cool electronics such as computer 74 through tubing 76. The heater and air conditioner are connected directly to the cabinet for analyzer 40 and computer 74 respectively.

The fundamental features of the system's optical design are illustrated in FIG. 2. Optical cell 54 consists of a single pass design using a one inch diameter fused silica (UV) windows 78 and 80. Fused silica windows 78 and 80 are glass blown onto cell body 82 which is made of quartz. Preferably, the length of cell body 82 depends upon the sensitivity to the measured analyte, measured range and the nature of the interferents, but is typically around 20 inches and inlet/outlet tubes 52 and 60 (½ inch glass tubing) are at opposite ends (i.e., in a "Z" configuration). A pair of fast off-axis parabolic mirrors 84 and 86 (1 inch diameter, 1 inch focal length) coated with magnesium fluoride, are positioned at each end of optical cell 54. Parabolic mirrors 84 and 86 are employed to allow optical interface between the various components and beam collimation throughout optical cell 54. The system is designed and constructed to be rugged and insensitive to mechanical vibrations once aligned.

Optionally, a multi-pass cell could be used instead of the single-pass design making even longer optical path lengths readily accessible. Explanation of White Cell (e.g., Infrared Analysis, Inc.) is included. Other types of multi-pass cells are also available commercially (e.g., Astigmatic cell by New Focus, Inc.)

Parabolic mirrors 84 and 86 could be dispensed with altogether by using a "light tube" design. Entire optical cell 54 would be made of a fused silica (UV grade) and coated externally with magnesium fluoride and a reflective material (e.g., polished aluminum). The diameter and length of the reflective light tube design would depend upon the particular application. A radiation source 88 would be placed close to the entrance of optical cell 54 and a CCD (charge couple device) array spectrometer 90 directly at the opposite end, or exit of optical cell 54. No lenses or mirrors would be necessary. Varying the angle of radiation source 88 to optical cell 54 would change the number of reflections the light beam would make inside the cell, thereby changing the distance traveled by the beam. The effective optical path length of such an arrangement would be longer than the physical length of the cell, thereby raising the instrument sensitivity. This is because the UV absorption characteristics of a gas are directly related to path length as defined by the Beer-Lambert Law. Undesirable radiation would be filtered out with bandpass filters (not shown).

In the optical cell and detecting system of FIG. 2, radiation from source 88 is reflected off parabolic mirror 84 and through sample flowing in the opposite direction, as indicated by arrows 93 and 95 respectively. Light beam 95 then reflects off parabolic mirror 86 into CCD array spectrometer 90. The output of CCD array 90 is then connected to an analog digital converter for analysis by a program to be described in greater detail hereinafter.

Radiation source 88 is preferably a xenon flash lamp such as an EG&G 11C Series (FX1152) along with the supply trigger module and power supply. This lamp has a strong emission in the desired spectral range (180–300 nm) is very stable from pulse to pulse and has a long lifetime (typically $10^9$ flashes). Another advantage of this source is that typical emission peaks from the excited xenon gas can be used to calibrate the detector and test optical resolution of the system. Source 88 is triggered directly from controlling software in computer 74, also controlling spectrometer 90 thereby synchronizing energy pulses from source 88 with measurements. Source 88 could be an alternative source such as a deuterium lamp, mercury lamp, mercury/argon lamp, tungsten halogen lamp, diode laser, helium-neon laser, etc. if desired.

CCD array detector 90 is a miniature spectrometer such as an ocean optics S1000 miniature spectrometer having a dispersing element (holographic grating, 2400 lines per mm) equipped with a 25 micron ($\mu$m) slit and a 1024 element array of Si CCD detectors. The measurement range employed is from 180 to 300 nm. One or more of miniature spectrometers 90 can be added on in a modular fashion to increase the measurement range without sacrificing optical resolution and/or to act as a reference channel. All 1024 coupled elements of detector array 90 receive their respective wavelengths of radiation effectively simultaneously so that time-related effects of the sample flowing through optical cell 54 will not introduce inaccuracies into the measurement.

In certain applications, a detector array 90, from other manufacturers may be more suitable. For example, they may have a higher dynamic range, different detector element composition and could be substituted if desired.

Cabinet 70 (FIG. 1) also includes programmable logic controller 92 (PLC) linked to computer system 74 that controls mechanical parts (e.g. pump 58 and solenoid valves 32, 46 and 50). Program logic controller 92 also controls the temperature of heated line 36, and the interior of instrument enclosure or cabinet 40. Air conditioner/heater 72 maintains the temperature inside cabinet 40 and instrument enclosures to within +/−1° C. and constantly circulates air. A filter (not shown) between heater and air conditioner 72 and lines 66 and 76 destroys any ozone generated by the source. Industrial personal computer 74 digitizes analog signals from miniature spectrometer detector array 90 and sends the required values to data acquisition system 94 through serial link 96 in cabinet 70.

Data acquisition system 94 (DAS) operates under custom data acquisition system software that is written to accommodate the requirements of the analyzer. The program is written to run in the environment of a personal computer.

Equation (A) expresses mathematically how the custom data acquisition system software analyzes the data for analyte (A). An analyte is a chemical species and may be either an atom, molecule, radical or ion in a fluid which can be gaseous or liquid.

$$SR(A) = \sum_{n=1}^{x} S(M_n)/[\sigma_n * S(R_n) + (1 - \sigma_n) * S(R_{n+1})] \quad (A)$$

where, x=corresponds to the number of measurement points for analyte A,

SR(A)=the signal ratio for analyte A, $S(M_n)$=the signal strength, in arbitrary units (e.g., electronic counts, volts, absorbance units, % transmission) of the nth measured point in the spectrum corresponding to an absorption peak of analyte A, $S(R_n)$=the signal strength, in arbitrary units (e.g., electronic counts, volts, absorbance units, % transmission) of the nth reference point in the spectrum of analyte A, σn=constant adjusting the nth signal ratio for baseline effects.

A polynomial regression algorithm derived from experimental data according to Equation (A) is used to calibrate the instrument response to the concentration of analyte A to calculate the concentration of analyte A without modeling spectral interferents. The algorithm is derived from experimental data using Equation A shown above.

The algorithm of the equation A is used to calculate a signal ratio for the particular analyte thus minimizing spectral interferences. A second algorithm is developed from known concentrations of an analyte that are plotted on a graph with the signal ratio as the x-axis and the concentration as the y-axis. Multiple signal ratios are calculated using four or more concentrations of the analyte. The graph is then used to derive an algorithm from a polynomial regression or other statistical method using points on the graph. The computer will now have a learned response for a range of concentrations of the analyte.

A third algorithm is then developed by plotting the concentration of an interferent against the instrument response (signal ratio) for the desired analyte. The algorithm is derived from a polynomial regression or other statistical method and can be used to model for the interferent in the data processing software. This method can be used to compensate for one or more interferents as each interferent will have an associated experimentally derived algorithm.

In the so-called "decision-matrix" an array of algorithms is used to model the interaction of one or more interferents more precisely. For instance, analyte A is blended with interferent B at a specific concentration of A. The signal ratio of A is noted as a function of B and plotted. This will lead to an algorithm, derived through a polynomial regression or other statistical method, which is specific to a window of interaction of B with A. The procedure is repeated for a variety of concentrations of A with B. The procedure is repeated for a variety of concentrations of A and B until the measured range of A has been covered adequately (usually, five concentrations suffice). The process is repeated for other interferents. The library of algorithms mathematically describing the interferents of one or more species with the signal for analyte A is stored in the data processing software.

Computer and DAS 94 have now been taught the algorithms to determine the concentration of an analyte, concentration of interference and the interaction of interference over a wide range providing a decision matrix for use to analyze liquids or gases having an unknown concentration of an analyte. While it is possible to perform these procedures with each analyzer, it is generally not necessary as the experimentally developed algorithm learned by the computer will not change for the analyte or interferents in question.

A second experimentally derived polynomial regression algorithm is used to measure the concentration of one or more interferences to make up the corresponding adjustments to the previously calculated concentration of analyte A. A decision matrix uses the measured concentration of one or more interferents to select an appropriate polynomial regression algorithm derived experimentally to "fine tune" the missing concentration of analyte A. The acquired data can be further manipulated by applying corrections for sample dilution caused by oxygen and water vapor, statistical smoothing of the data can also be applied at this stage.

Figure 3:
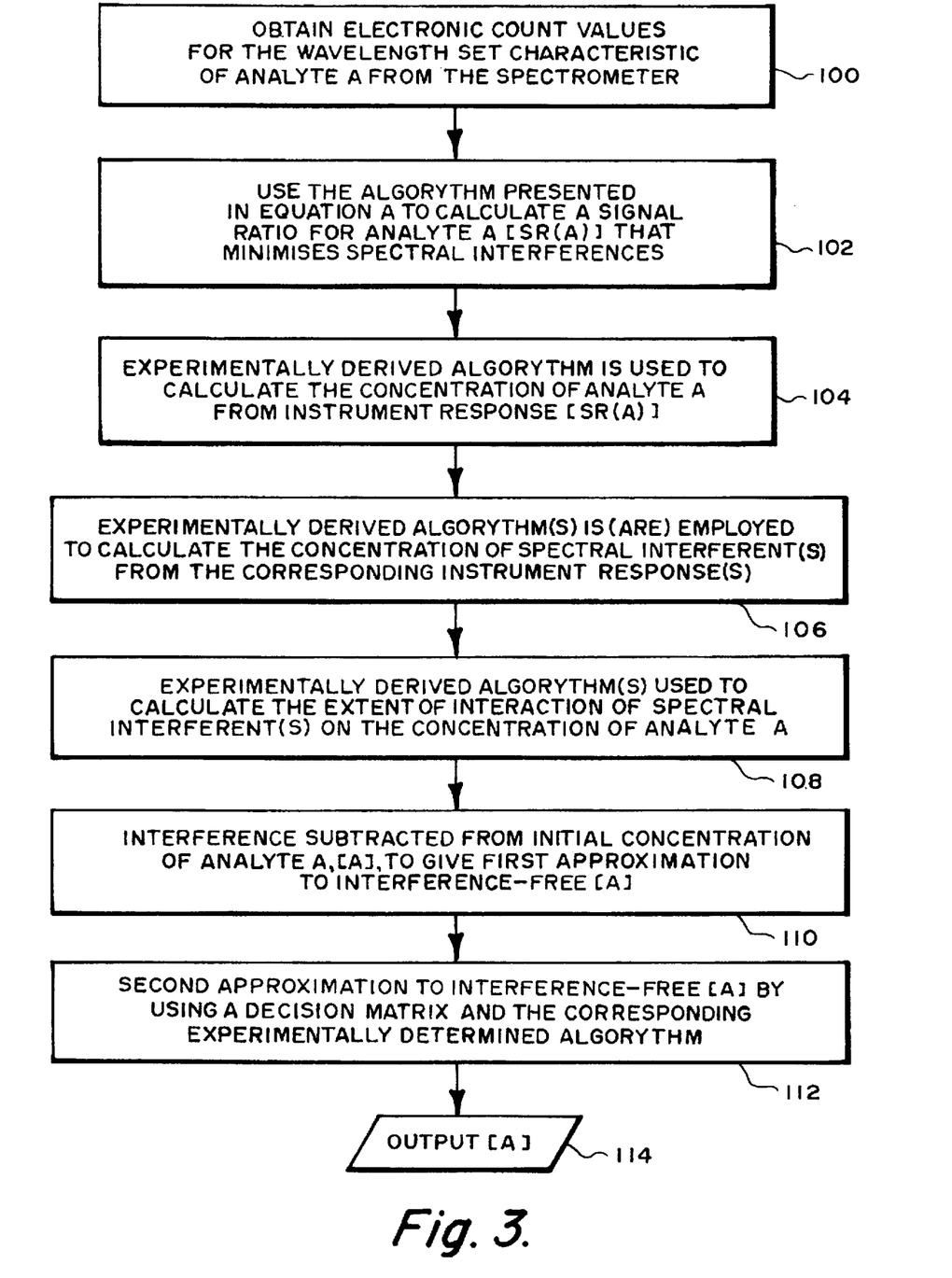
FIG. 3 is a flow chart illustrating processing of the sample data in the liquid and gas analyzer according to the invention.

The calibration approximations and mathematical manipulations of the computer program executed in PC 94 are illustrated in flow diagram of FIG. 3. The first step is the receipt of electronic count values of the wavelength's set characteristic of analyte A obtained from spectrometer 90 in a subroutine 100. Subroutine 102 then uses the algorithm derived from Equation A to calculate a signal ratio for the analyte that minimizes spectral interference. Subsequently subroutine 104 calculates the concentration of analyte A from instrument response. The concentration spectral interference from corresponding instrument responses are then calculated in step or subroutine 106 which then proceeds to calculate the extent of interaction of spectral interferents on the concentration of analyte A (Subroutine 108). Subroutine or step 110 then subtracts the interference from the initial concentration of analyte A to provide a first approximation to interference-free analyzer.

Subroutine or step 112 can be used to improve the modeling of an interference-free concentration of analyte A by performing a second approximation by using a decision matrix and a corresponding experimentally determined algorithm. The system through the sophisticated modeling described then provides an output 114 that is an extremely accurate measurement of low levels of the analyte which can be used in a environmental monitoring and process control.

It has been found that in instances when high concentrations of interference are present (e.g., 2 ppm $NH_3$ in the presence of 1,000 ppm $SO_2$) further mathematical treatment may be necessary. Multiple derivative spectroscopy (e.g., second derivative of absorption with respect to wavelength) and/or fast Fourier transforms are commonly used to overcome these difficulties and the data acquisition system is designed to link to standard software packages that can perform these operations.

Figure 3A:
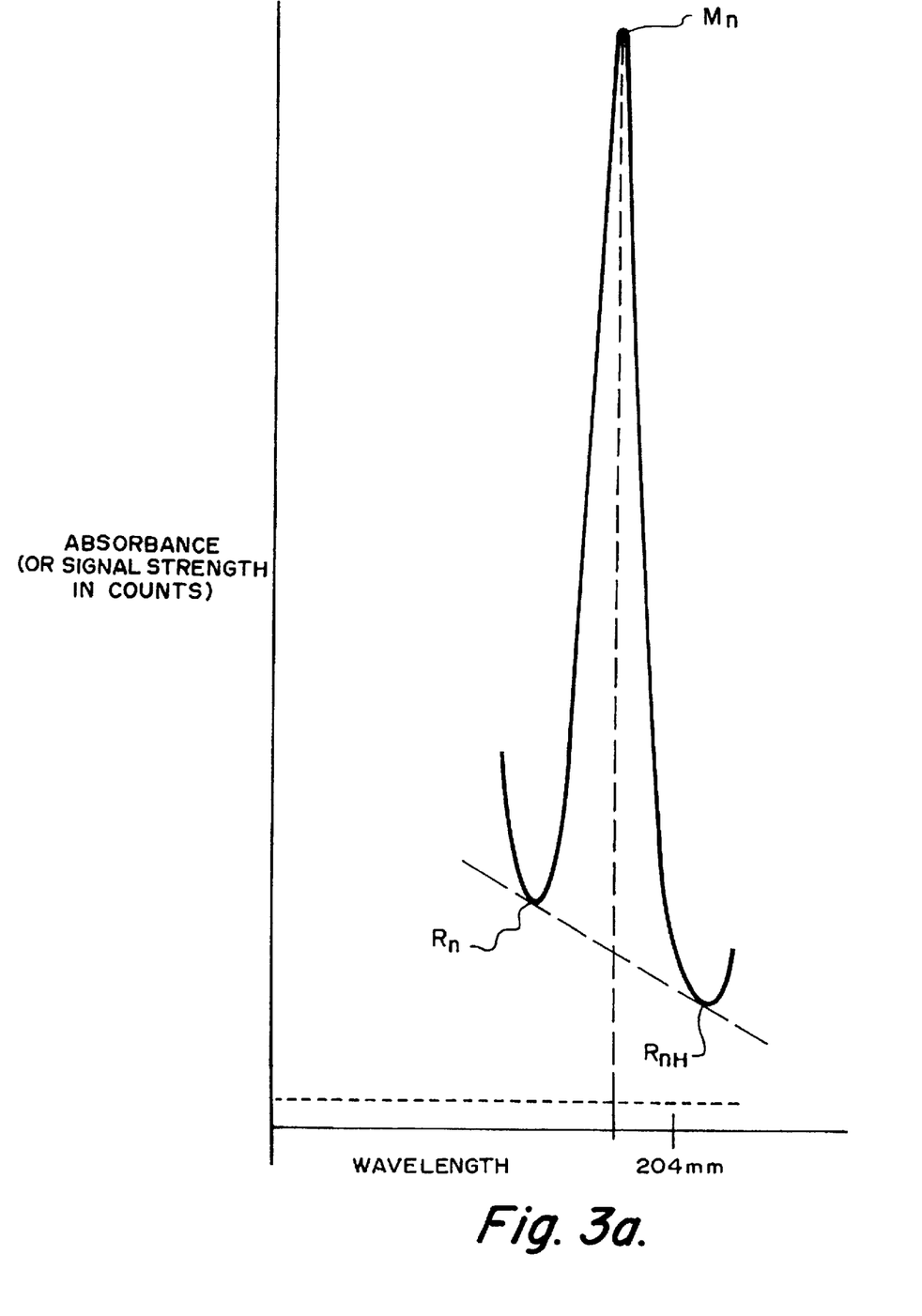
FIG. 3(a) is a graph of the absorbance spectrum of an analyte.

The algorithms referred to in the flow diagram of FIG. 3 are determined by measuring points on an absorbance spectrum visible on the display in computer 94 (i.e., PC in FIG. 1). For example the signal ratio of an analyte A can be calculated [i.e., SR(A) in Equation (A)] from an absorption spectrum on the display received from the spectrometer as shown in FIG. 3(a) or from a corresponding transmission spectrum (inverted absorbance spectrum) using Equation (A). The spectrometer display can also be in the "scope mode" representing the UV source emission as well as other effects (e.g., differing detector performance in the array and optical effects such as reflections and absorption by the optical medium). This eliminates the need for running a background spectrum as referencing is done in the algorithm. Points $M_n$, $R_n$, and $R_{n+1}$ are determined experimentally and $\sigma$ is calculated using the following equation.

$$\sigma_n = \frac{(R_{n+1} - M_n)}{(R_{n+1} - R_n)} \quad \text{(B)}$$

Where:

$M_n$ is the measured wavelength and represents the absorbance maximum.

$R_n$ and $R_{n+1}$ represent two reference points selected for each $M_n$.

The spectrometer is calibrated for analyzer response as a function of concentration of analyte "A" both with a non-absorbing carrier (e.g. nitrogen) as well as in the presence of an interferent. The decision matrix is a matrix of calibration data determined experimentally, mathematically linking interferent concentrations with the concentrations of analyte "A". The program automatically selects the appropriate algorithm previously derived, to be used from the first approximation of the concentration of analyte "A" (110 in FIG. 3) to refine the measurement. For example, assume the analyzer determines via the first approximation of the concentration that the level of an analyte such as ammonia is around 5 ppm with an interferent concentration of sulfur(IV) oxide of 30 ppm. The program then selects the closest interferent algorithm, previously derived as discussed above, for example, the algorithm for a concentration of 0–100 ppm of sulfur(IV) oxide at 6 ppm of ammonia. The program then determines the extent of the interaction which it can now subtract from the concentration of ammonia to give "fine tuned" (i.e. very accurate) results, such as 4.8 ppm.

Figure 4:
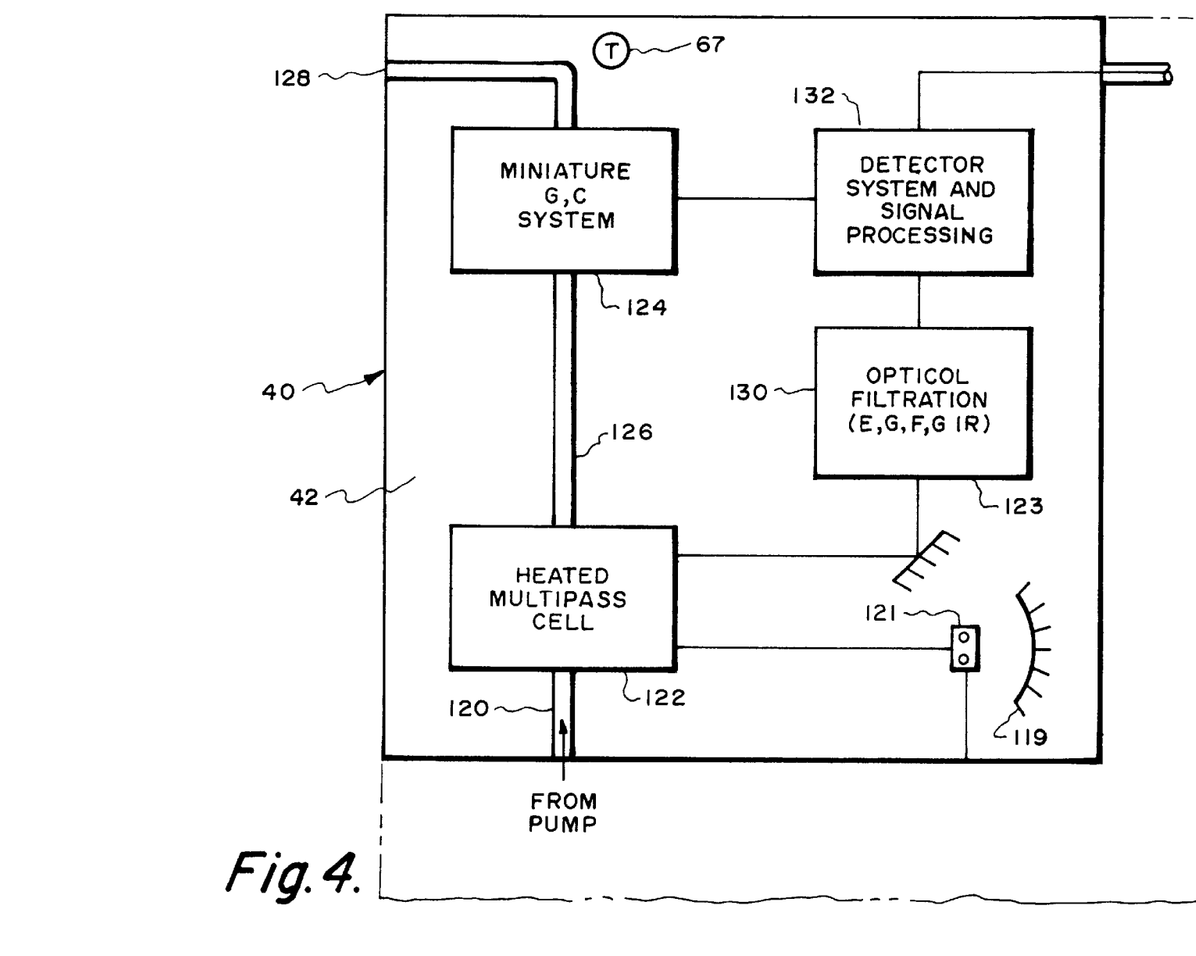
FIG. 4 is a diagrammatic view of the system illustrating the modular construction and how an infrared (IR) analyzer module can be easily interfaced with the liquid and gas analyzing system according to the invention.

A unique and valuable advantage of the analyzing system is a design that permits modular integration of other components. Chamber 42 in analyzer cabinet 40 can be used, for example, to add an infrared (IR) analyzer module that can be easily interfaced with the above system, as shown in FIG. 4. Instead of exhausting through port 64, the exhaust of pump 58 will be fed through conduit 120 to heated multi-pass cell 122 (e.g., White Cell supplied by Infrared Analysis Inc. and/or Astigmatic cells available from New Focus Inc.) and then either connected to a miniature gas chromatographic instrument 124 by heated line 126 which will be described hereinafter, vented through port 128 to the atmosphere, or recirculated back to stack 10. Source comprised of mirror 119 and light source 121 irradiates the sample in multi-pass cell 122 which is reflected by mirror 123 to optical filtration system 130 and detector 132 for analysis. The principle of operation of the IR system in chamber 42 of analyzer cabinet 40 as a component of the system consists of a multi-gas non-dispersive infrared (NDIR) analyzer such as that disclosed and described in U.S. Pat. No. 4,746,218 of Lord issued May 24, 1988 incorporated herein by reference. The source could also consist of a glowing ceramic element (from Oriel Corporation), a diode laser and/or a carbon dioxide laser.

Gas filtration and detection system 130 and 132 could be replaced by a dispersive Fourier Transform (FT) spectrometer using a mercury cadmium telluride or indium antimonide detectors. Other systems that could be used are a rotating diffraction grating mounted to a synchronized motor such as one (available from Reese Instruments Inc.) optically coupled to a detector of choice, a linear circular variable filter (available through Optical Coating Laboratories Inc.) mounted to a digitally controlled stepper motor and aligned with a detector of choice, a system employing photo acoustic spectroscopy or an opto-acoustic filtration system with an appropriate detector.

The heated gas stream from pump 58 can be fed to the heated multi-pass cell 122 as described previously, and then through heated line 126 to a miniature gas chromatographic (GC) instrument (available from Microsensor Technology, Inc.) can easily be linked into the system either instead of, or along with the IR capabilities described above. Gas chromatographic instrument 124 is connected in parallel with sample line 26 and is programmed to sample from the gas stream at regular intervals. The design of the system, allowing a modular approach, makes the entire analyzing system highly versatile and powerful. The added capability of performing multiple analyte measurements, both in the IR and the UV spectrum in a single analyzer, is a unique feature of the system that is unparalleled in the industry. This modular construction also enables the interrogation of one or more miniature gas chromatographic instruments and further increases the analyzer's usefulness.

The invention described herein is the only industrial continuous emission monitoring system that can operate well below 200 nm in the UV spectrum. The system operates in the spectral range between 180 and 300 nm; this extension of 20 nm from 200 to 180 nm compared with traditional analyzers, enables the spectroscopic access to a series of strong peaks characteristic of a variety of analytes such as NO and $NH_3$.

Fiber optics may be used if the analyte has appropriate absorption bands at wavelengths above 200 nm (e.g., $SO_2$, COS, $NO_2$ and $Cl_2$). The mathematical treatment used here, such as the analysis employed to calculate the signal ratio of an analyte and the decision matrix to refine interference compensation, substantially differ from those commonly used. Most UV based analyzers employ a deuterium source, whereas a special state of the art xenon source is used here. These methods provide distinct advantages that were discussed previously.

The system described above can also be easily converted into an ambient air quality analyzer to measure parts per billion (ppb) levels of a host of analytes (e.g., ozone, nitrogen (II) oxide, nitrogen (IV) oxide, benzene and toluene). The main modification would be in the sampling system which would not require heating to 250° C. Maintaining the gas sample at 10° C. above ambient would be sufficient. The optical cell design may preferably include a multi-pass arrangement (e.g., White Cell or Astigmatic cell) to generate sufficiently long path lengths for the required concentration ranges. The signals are processed and displayed in the data acquisition system in the fashion previously described.

Data acquisition system 94 is a personal computer running under an environment such as a Windows operating system having a graphic display such as commercially available from Quinn-Curtis to plot concentrations of desired analytes versus time. The program logs data to a storage medium such as a hard disk or floppy disk and allows historical data to be readily accessed and displayed graphically on the screen.

Non-invasive gas analysis of industrial streams (e.g. gas stacks) is also possible using the technology described and discussed above. The system design is summarized in the schematic diagram of FIG. 5. A single or double pass configuration is feasible and depends upon stack diameter and the required instrument measurement range. A single strand fiber 136 is interfaced with light source 138 and mounted in cabinet 140 having a power supply 142, a CCD array spectrometer 144 and an industrial PC 146 are connected by cable 148. The end of fiber 136 is fitted with collimating lens 150 which is mounted to project a beam across stack 152 where it is collected by a suitable lens 154 and focused onto a second fiber 156 which is coupled to CCD array spectrometer 144.

Figure 5:
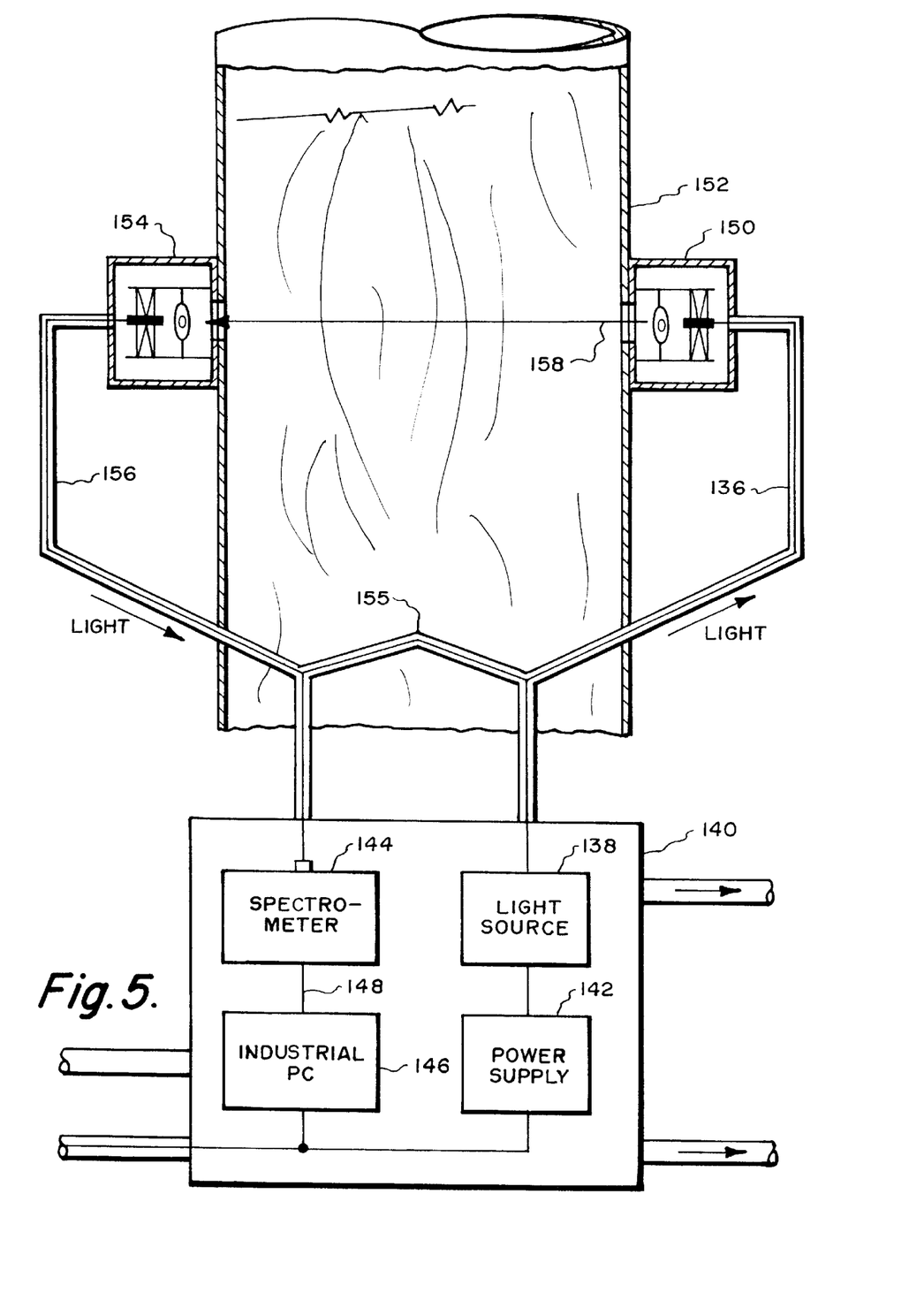
FIG. 5 is a diagram illustrating, in schematic form, the system of the invention modified for non-invasive gas analysis of industrial waste streams (e.g. gas stacks) with the liquid and gas analyzer according to the invention.

In a double pass configuration, light beam 158, passing through stack 152 would be reflected by a retro-reflective mirror (aluminum coated with magnesium fluoride for the UV) whereas the retro-reflective mirror, where the light is collected onto fiber 156, plugged into spectrometer 144. Restraints imposed on fiber materials would limit the measurement range of such an analyzer from 200 nm to greater than 1 microns ($\mu$m). The signals are processed by the data acquisition system illustrated in FIG. 1 in the same manner as previously described.

Referencing of the signal can be achieved by an additional fiber 155. A signal ratio can be obtained in real time employing spectrometer 144 and switching between reference fiber 155 and measurement fiber 150. A corrected signal ratio can be obtained in real time if the measurement fiber 138 is connected to a master spectrometer and reference fiber 155 connected to a slave spectrometer.

The instrument disclosed and described is also capable of operating in an "emission mode" where one or more multiple flames (e.g., utility boilers) can be measured and monitored through emission spectroscopy. This method would employ a similar approach as in the "absorption mode" utilizing equation A and related algorithms. An important application of this technology would be for utilities to meet upcoming $NO_X$ control requirements as described in the publication "Wanted: Advance Instrumentation To Help Clean Air", Robert Iverson & Joseph Weiss, Intech April 1995, pages 79 through 83.

The emission spectrum of a flame is characteristic of its temperature and therefore, can be used as a control system to adjust the air/field ratio at individual burners so that all operated at a fixed temperature. For this application a system similar to that shown and described with respect to FIG. 5 would be used either with or without optical fibers. A flame or other emission (e.g., hot flue gases) provides the source which will be monitored and measured by spectrometer 144. Equation A and the associated algorithms would then be used to analyze the flame in a manner similar to that disclosed in U.S. Pat. No. 4,043,742 issued to Lord et al, May 17, 1976 incorporated herein by reference. This patent relates to the monitoring of radiation emissions (e.g., analysis of flames).

The system disclosed and described hereinabove can also be easily adapted to measure low levels of analytes in solutions (either in the aqueous phase or dissolved in an alternate liquid medium not absorbing in the measurement range such as hexane). A filtered sample is channeled to analyzer 40 via inert materials and lined, commercially available, solenoid valves lined with inert material. Optical cell 54 is used as with sample gases, except a much shorter path length is now required. Heated pump 58 would be replaced with a peristaltic pump or other suitable alternative. In most cases, use of optical fibers is desirable. Signals from the system for processing a solution are processed and displayed in the data acquisition system as described hereinabove.

The system illustrated in FIG. 5 could also be employed as a single-pass system with the exception of choice of particular fiber optic material probes that are exposed to the measured medium for in-situ liquid analysis for environmental monitoring. The signals would then be processed and displayed in the data acquisition system in the fashion described hereinabove.

Long path/remote sensing gas monitoring (e.g., fence line monitoring and leak detection) can be achieved with the system essentially identical to the analyzer described with respect to FIG. 5. The objects necessary to prepare the radiation for projection over long paths, running typically several hundred meters, would be modified. A telescope and retro-reflective arrangement can be used to obtain satisfactory results. An enclosure fitted with a system such as that disclosed in FIG. 5 with appropriate optics for projection over long paths, could detect leaks in a storage tank. The signals would then be processed in the data acquisition system as described hereinabove.

The system described with respect to FIG. 1 with the exception of the probe, could also be employed in the biomedical industry to yield a versatile, low cost, non-invasive diagnostic system having great potential. For example, a breath analysis system could be provided to analyze the breath of people for diagnostic purposes. The breath of healthy human beings and animals normally contain approximately 60 to 80 volatile compounds produced by endogenous metabolic and catabolic reactions. Individual breath components yield valuable information regarding certain diseases and toxic end points that can be valuable diagnostic tools. Expired breath analysis are described in a number of areas in the literature. For example CO monitoring in premature infant breath infected with hyperbilirubinemia or hemolytic disease can be used as an index of bilorubin production. Statistics on measured data can help predict whether the neonate is likely to develop potentially dangerous jaundice or not.

The system could also be used for non-invasive evaluation of the nutritional status and body composition in pediatric patients for monitoring exhaled $^{13}CO_2$, following bolus administration of $NAH^{13}CO_3$ urea and $^{14}C$ and $^{13}C$-analysis in exhaled breath, follow ingestion of suitably labeled compounds are commonly used to determine the presence of Heliobacteria in the stomach duodenum. This pathogen is implicated as a cause of recurrent duodenal ulcers. Current breath analysis techniques have severe restrictions; $^{14}C$ is radioactive and $^{13}C$ analysis requires a mass spectrometer. Patients with pneumonia, COBD exacerbation, cystic fibrosis, undergoing CABG, sclerosis and intravenous nitroglycerine and nitroprusside show uncharacteristic NO levels on their exhaled breath which can be measured with the system of the present invention. The system is also useful for non-invasive toxological assessment following chemical administration to laboratory animals.

Figure 6:
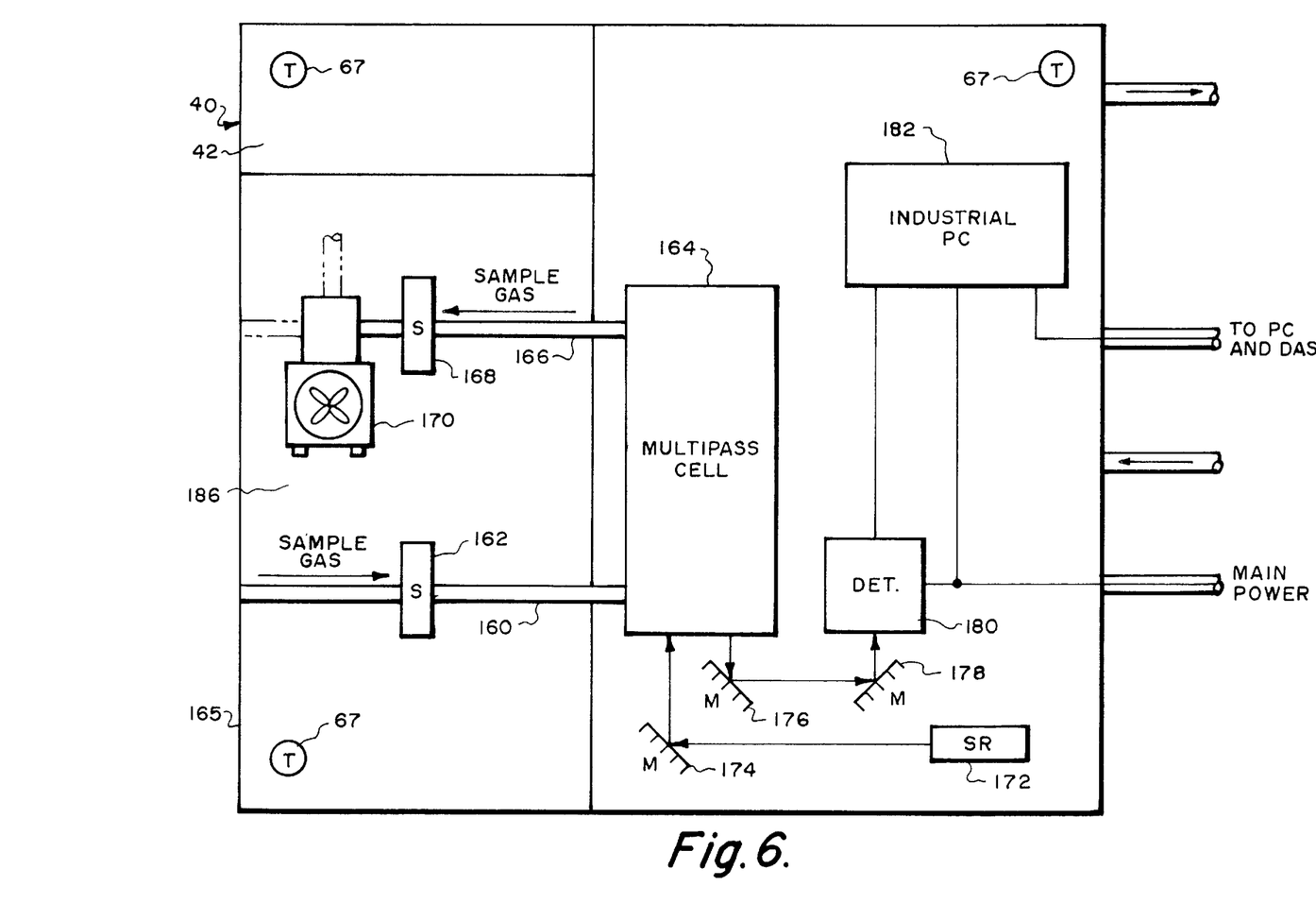
FIG. 6 is a diagram of an embodiment of the system for use in the medical field for non-invasive human breath analysis.

A breath analysis system is disclosed and described in the schematic diagram of FIG. 6. Sample handling temperatures around 40° C. would be desirable. Pass-through and re-breathing systems are commonly employed to collect breath samples. A sample can be collected in a sterile sealed bag made of a neurosynthetic material fitted with a suitable valve. The bag is filled with exhaled breath by the patient and the valve is then connected to inlet 165 of analyzer 40 for sampling. This system would use static sampling rather than dynamic sampling as described with the stack sampling system hereinabove. That is, the sample is collected and then the system is isolated by means of a miniature solenoid valve. The gas mixture is analyzed and purged with zero gas. Multiple measurements are possible in a short period of time for one sample of breath, therefore allowing an internal check of the measured concentration of the toxic analyte.

The gas sample is then fed to the system through conduit 160 and solenoid value 162 to multi-pass cell 164 and exhausted through conduit 166, solenoid 168 and pump 170. Radiation source 172 is reflected off parabolic mirror 174 into multi-pass cell 164 and back out off parabolic mirrors 176 and 178 to CCD detector array 180 as before for processing by industrial PC 182. The signal out from industrial PC 182 at 184 is processed by the data acquisition system as before.

A more elegant sampling method can have the patient breathing directly into inlet 165 of analyzer 40 through conduit 160 with pump 170 being a low power pump to ensure adequate sample turnover rates and to draw a zero gas through the system once measurements have been made. The described system is capable of measuring multiple components of a breath sample and a complementary IR module in chamber 186, as described hereinabove, is desirable in many applications to monitor analytes that do not have suitable UV absorption band (e.g., CO, $^{12}CO_2$ and $^{13}CO_2$). This may be useful in obtaining higher volume samples that could then be analyzed through astigmatic multi-pass cell at high path lengths and increase sensitivity.

The system could also be adapted for analysis of human fluids such as saliva, human blood and urine with modifications. Human saliva contains a variety of compounds that as in the case of human breath, have a variety of applications for non-invasion diagnostics. Also, human blood has a well-documented history of diagnostic value. For these applications, the proposed system closely resembles the system disclosed in FIG. 5 with the exception that no sampling system is required, as all measurements are made in a static mode. A sample of human fluid such as saliva, blood or urine is transferred into a disposable cell and inserted into a provided slot in analyzer 40. Preferably, for blood analysis, the sample would require anaerobic handling. The cell is plugged between the source fiber optic 136 (FIG. 5) and the collecting fiber optic strand 156 for delivery to CCD array spectrometer 144. In this embodiment, stack 152 would simply be a housing having a slot for receiving the cell containing the sample. Alternatively, optical fibers could be dispersed with altogether and the light beam directed with reflective optics such as those shown in FIG. 2.

Thus there has been disclosed a liquid and gas analyzing system with improved efficiency by shortening the sample path and eliminating contamination that can effect the analyte in a sample. The system has many applications in addition to environmental monitoring process controls such as in the biomedical industry and monitoring of liquid samples.

This invention is not to be limited by the embodiment shown in the drawings and described in the description which is given by way of example and not of limitation, but only in accordance with the scope of the appended claims.

What is claimed is:

1. A spectroscopic method of measuring an analyte in a gas or liquid sampled at a source comprising;

constructing sampling means of a material inert to said sample of a gas or liquid;

mounting said sampling means at the source of said gas or liquid;

collecting a sample of said gas or liquid;

delivering a sample of said gas or liquid from said sampling means to an analyzer optical cell mounted at the source of said gas or liquid;

irradiating said sample with a source of radiation;

detecting radiation from said sample with a spectrometer having an array of at least two detectors to produce data;

calculating a signal ratio for said analyte that minimizes spectral interferences from the equations:

$$SR(A) = \sum_{n=1}^{x} S(M_n)/[\sigma_n * S(R_n) + (1 - \sigma_n)*S(R_{n+1})] \quad (A)$$

$$\sigma_n = (R_{n+1} - M_n)/(R_{n+1} - R_n) \quad (B)$$

where:

x=the number of measurement points for analyte A,

SR (A)=the signal ratio for analyte A,

S ($M_n$)=the signal strength of the nth measured point in the spectrum corresponding to an absorption peak of analyte A, S ($R_n$)=the signal strength of the nth reference point in the spectrum of analyte A, Mn=chosen measured wavelength, Rn, Rn+1=reference points selected for each measured $M_n$, σn=constant adjusting the nth signal ratio for baseline effects, calculate the concentration of said analyte from responses received during said detection;

calculate the concentration of spectral interferents from the responses received from said detection using said equations (A) and (B);

calculate the extent of interaction of spectral interferents on the response of said analyte;

subtracting said interferent interactions calculated to provide a first measurement of said analyte with reduced spectral interferences;

iterative processing of said first measurement through a decision matrix of calibration data to provide a refined second accurate measurement of said analyte;

whereby an accurate measurement of said analyte with substantially reduced spectral interferents is made.

2. The method according to claim 1 in which said sampling means construction includes a probe having a replaceable inert interior surface; and collecting said sample by mounting said probe in the path of said sample.

3. The method according to claim 2 in which said sampling means construction includes a solenoid valve constructed of an inert material.

4. The method according to claim 1 wherein said construction of said sampling means comprises; constructing a probe having an inert replaceable liner; mounting said probe in a sample path; connecting a synthetic inert T-union to said probe exterior of said sample path; connecting a flexible tubing of inert synthetic material to an outlet of said T-union; connecting an analyzer to said flexible inert tubing.

5. The method according to claim 4 in which said flexible tubing is formed in a spiral to minimize stress on said analyzer components.

6. The method according to claim 5 including connecting a high temperature solenoid valve having an inert liner between said T-union outlet and said flexible tubing.

7. The method according to claim 6 including connecting said flexible tubing to an inert glass line in said analyzer.

8. The method according to claim 7 including connecting an inert glass solenoid valve between said flexible tubing and said glass line; said glass line being connected to deliver said sample to said optical cell.

9. The method according to claim 8 including connecting an inert quartz T-piece between said flexible tubing and said glass solenoid valve; connecting a blow-back solenoid valve to said T-piece; whereby compressed air can be periodically used to clear said probe of particles.

10. The method according to claim 1 in which said sampling system construction has a volume of less than about one liter; whereby analyzer response times are minimized.

11. The method according to claim 1 comprising irradiating said sample in said optical cell with a xenon flashlamp.

12. The method according to claim 1 comprising irradiating said sample in said optical cell with a UV source selected from the group consisting of a mercury/argon lamp, a deuterium lamp, a mercury lamp, a tungsten lamp, a diode laser, and a helium neon laser.

13. The method according to claim 12 including detecting said radiation with one or more CCD detectors having an array of detector elements.

14. The method according to claim 13 including detecting said radiation with said one or more CCD detectors having an array of 1024 detector elements to prevent time related inaccuracies.

15. The method according to claim 14 including detecting said radiation with a plurality of CCD detector arrays to increase the measurement range.

16. The method according to claim 1 including deriving an algorithm experimentally to calculate the concentration of said analyte from instrument response.

17. The method according to claim 16 in which said concentration of spectral interferents is calculated by deriving one or more algorithms experimentally from corresponding instruments responses.

18. The method according to claim 17 in which the extent of interaction of spectral interferents is calculated by deriving one or more algorithms experimentally from the calculated concentration of spectral interferents.

19. A system for measuring an analyte in a gas or liquid sampled at a source comprising;
   sampling means constructed of materials inert to a sample of a gas or liquid;
   mounting means for mounting said sampling means at a source of said sample;
   said sampling means comprising;
      a probe having an inert replaceable interior;
      an inert flexible tubing connecting said probe to an analyzer;
   an optical cell in said analyzer receiving said sample;
   irradiating means for irradiating said sample in said optical cells;
   a spectrometer having an array of at least two detectors for detecting radiation from said sample to produce data;
   data acquisition and processing means receiving and processing said data, said data acquisition and processing means comprising;
      signal ratio calculating means calculating the signal ratio of said analyte that minimizes spectral interferents from the equations;

$$SR(A) = \sum_{n=1}^{x} S(M_n)/[\sigma_n * S(R_n) + (1 - \sigma_n) * S(R_{n+1})] \quad (A)$$

$$\sigma_n = (R_{n+1} - M_n)/(R_{n+1} - R_n) \quad (B)$$

where:
   x = the number of measurement points for analyte A,
   SR(A) = the signal ratio for analyte A,
   $S(M_n)$ = the signal strength of the nth measured point in the spectrum corresponding to an absorption peak of analyte A,
   $S(R_n)$ = the signal strength of the nth reference point in the spectrum of analyte A,
   Mn = chosen measured wavelength,
   Rn, Rn+1 = reference points selected for each measured $M_n$,
   σn = constant adjusting the nth signal ratio for baseline effects,
   concentration calculating means calculating the concentration of said analyte,
   spectral interference calculating means for calculating the concentration of spectral interferents from the response received using said equations (A) and (B);
   interaction calculating means calculating the interaction of spectral interferents on the response of said analyte,
   subtracting means subtracting said interferent interaction from the response of said analyte to provide a first measurement of concentration of said analyte,
   iterative processing means for processing said first measurement through a matrix of calibration data to provide a refined second accurate measurement of said analyte;
   whereby an accurate measurement of said analyte with substantially reduced spectral interferents is made.

20. The system according to claim 19 in which said optical cell comprises; an inert quartz tube; inert fused silica windows on each end of said inert quartz tube; and inert glass inlet and outlet tubes at opposite ends of said inert quartz tube.

21. The system according to claim 20 in which said irradiating means comprises; a source of radiation; and reflecting means for reflecting said irradiation through said inert quartz tube.

22. The system according to claim 21 in which said irradiating means comprises an ultraviolet radiation source.

23. The system according to claim 22 in which said ultraviolet irradiating source is a xenon flashlamp.

24. The system according to claim 22 in which said reflecting means comprise; fast off-axis parabolic mirrors at each end of said inert quartz tube.

25. The system according to claim 22 in which said reflecting means comprises; a reflective coating on said inert quartz tube.

26. The system according to claim 22 in which said ultraviolet source of radiation is selected from the group consisting of a deuterium lamp, mercury lamp, mercury/argon lamp, tungsten halogen lamp, diode laser, and a helium neon laser.

27. The system according to claim 19 in which said probe is comprised of a stainless steel sheath; an inert replaceable quartz liner inside said stainless steel sheath; filter means mounted on the tip of said probe; and heating means between said quartz liner and said steel sheath.

28. The system according to claim 27 in which said sampling means includes inert connecting means connecting said probe to said analyzer, said inert connecting means comprising an inert synthetic T-union connected to the end of said probe external to a source of said sample, and an inert flexible tube connecting said T-union to said analyzer.

29. The system according to claim 28 in which said inert flexible tubing is formed in a spiral to minimize stress on said analyzer components.

30. The system according to claim 29 including a high temperature solenoid valve having an inert line between an outlet on said T-union and said flexible tubing.

31. The system according to claim 30 including an inert glass line in said analyzer connecting said flexible tubing to said optical cell in said analyzer.

32. The system according to claim 31 including an inert glass solenoid valve connected between said flexible tubing and said glass line.

33. The system according to claim 27 in which said detecting means comprises one or more CCD detectors having an array of detector elements.

34. The system according to claim 33 in which said array of detector elements comprises an array of 1024 detector elements to prevent time related inaccuracies.

35. The system according to claim 34 in which said one or more CCD detector arrays comprises a plurality of CCD detector arrays to increase the measurement range.

36. The system according to claim 19 wherein said sampling means has a sample volume of no more than about one liter.

37. The system according to claim 19 in which said sampling means has a sample line of no more than about ten feet.

38. The system according to claim 19 in which said probe comprises light conducting fibers for collecting an in-situ sample.

39. The system according to claim 38 in which said in situ sampling comprises; a first light fiber connected to a source to be sampled; a source of light interfaced with said first light fiber to project a beam through said sample source; a second light fiber receiving said beam; said detecting means being interfaced with said second light fiber.

40. The system according to claim 39 in which the beam projecting end of said first light fiber has a collimating lens, and the receiving end of said second light fiber has a lens focusing said beam on said second light fiber.

41. The system according to claim 40 in which said first and second light fibers are connected to a stack to sample a gas stream.

42. The system according to claim 41 in which said first and second light fibers are connected to a cell containing a liquid sample.

43. A spectroscopic method of measuring an analyte in a gas or liquid sampled at a source comprising;

constructing sampling means of a material inert to said sample of a gas or liquid;

mounting said sampling means at the source of said gas or liquid;

collecting a sample of said gas or liquid;

delivering a sample of said gas or liquid from said sampling means to an analyzer optical cell mounted at the source of said gas or liquid;

detecting radiation from said sample with a spectrometer having an array of at least two detectors to produce data;

calculating a signal ratio for said analyte that minimizes spectral interferences from the equations:

$$SR(A) = \sum_{n=1}^{x} S(M_n)/[\sigma_n{}^*S(R_n) + (1 - \sigma_n)^*S(R_{n+1})] \quad (A)$$

$$\sigma_n = (R_{n+1} - M_n)/(R_{n+1} - R_n) \quad (B)$$

where:

x = the number of measurement points for analyte A,

SR(A) = the signal ratio for analyte A, $S(M_n)$ = the signal strength of the nth measured point in the spectrum corresponding to an absorption peak of analyte A, $S(R_n)$ = the signal strength of the nth reference point in the spectrum of analyte A, Mn = chosen measured wavelength, Rn, Rn+1 = reference points selected for each measured $M_n$, σn = constant adjusting the nth signal ratio for baseline effects, calculate the concentration of said analyte from responses received during said detection;

calculate the concentration of spectral interferents from the responses received from said detection using said equations (A) and (B);

calculate the extent of interaction of spectral interferents on the response of said analyte;

subtracting said interferent interactions calculated to provide a first measurement of said analyte with reduced spectral interferences;

iterative processing of said first measurement through a decision matrix of calibration data to provide a refined second accurate measurement of said analyte;

whereby an accurate measurement of said analyte with substantially reduced spectral interferents is made.

* * * * *